United States Patent [19]

Szabo

[11] Patent Number: 4,891,356
[45] Date of Patent: Jan. 2, 1990

[54] PROTEINASE INHIBITORS FOR TREATMENT OF GASTROINTESTINAL ULCER DISEASE

[75] Inventor: Sandor Szabo, Brookline, Mass.

[73] Assignee: Brigham & Women's Hospital, Boston, Mass.

[21] Appl. No.: 73,668

[22] Filed: Jul. 15, 1987

[51] Int. Cl.$^4$ .................. A61K 35/22; A61K 35/14
[52] U.S. Cl. .......................................... 514/2; 514/19; 514/136; 514/292; 514/496; 514/557; 514/561; 514/566; 514/619; 514/628; 514/709; 514/711; 514/819; 514/925; 514/926; 514/927; 424/99; 424/101; 530/415; 530/416
[58] Field of Search ............... 424/99, 101; 514/2, 514/19, 136, 292, 496, 557, 561, 566, 619, 628, 709, 711, 819, 925, 926, 927; 530/415, 416

[56] References Cited

U.S. PATENT DOCUMENTS

| | | | |
|---|---|---|---|
| 3,912,704 | 10/1975 | Singh | 424/99 |
| 4,164,571 | 8/1979 | Bonfils | 424/177 |
| 4,276,284 | 6/1981 | Brown | 424/101 |
| 4,340,591 | 7/1982 | Lucotte et al. | 424/177 |

OTHER PUBLICATIONS

Miller, T. A., *Amer. J. Physiol.*, 245:G601 (1983).
Szabo, S., et al., *Science* 214:200 (1981).
Szabo, S., *Klin. Wochenschr.* 64, Suppl VII, 116-122 (1986).
Dupuy, O., et al., *Digestion* 31:165 (1985).
Mizui, T., et al., *Japan J. Pharmacol.* 33:939-945 (1953).
Ezer, E., *Digestion* 31:168 (1985).
Dupuy, D., et al., *Gastroenterology* 91:966-977 (1986).
Szabo, S., *Gastroenterology* 88:228-236 (1984).
Lichtenberger, L. M., et al., *Gastroenterology* 73:1072-6 (1977).
Andre, R., et al., *Amer. J. Physiol.* 247:G296-304 (1984).
Garner, A., *Scand. J. Gastroenterol.* 21:Suppl. 125, 203 (1986).
Szabo, S., et al., *Fed. Proc.* 45:Abs. 4873 (1987).

*Primary Examiner*—Mark L. Bell
*Attorney, Agent, or Firm*—Saidman, Sterne, Kessler & Goldstein

[57] ABSTRACT

A method of treating gastrointgestinal ulcer disease is provided which involves administration of a proteinase inhibitor or analogue to patients suffering from same. Of particular interest is the use of inhibitors of serine, cysteine, carboxyl, and metallo proteinases.

12 Claims, No Drawings

PROTEINASE INHIBITORS FOR TREATMENT OF GASTROINTESTINAL ULCER DISEASE

BACKGROUND OF THE INVENTION

1. Field of the Invention

The invention relates to a method of treating gastrointestinal ulcer disease in an animal comprising administering chemical inhibitors of the activities of enzymes that hydrolyze proteins, generically proteinase inhibitors.

2. Description of the Background Art

Nonspecific ulcers in the stomach and duodenum, commonly but inaccurately referred to as "peptic ulcers," affect about 10% of the population of the United States at least once in a lifetime. *Gastroenterology* 69:166–174 (1975).

Drug-induced (iatrogenic) ulcers are even more common. A large proportion of chronic users of aspirin and nonsteroidal anti-inflammatory drugs (e.g., patients with rheumatoid arthritis and osteoarthritis, and healthy people aiming for the prevention of disease) are affected by drug-induced ulcers in a dose- and time-dependent manner. Lanza, F.L., et al., *Amer. J. Gastroenterol.* 80:767–769 (1985); Lorenz, R.L., et al., *Lancet* 1:1261–1264 (1984).

"Ulcer disease," which is a more accurate designation than "peptic ulcer," is a mass disorder because, just as in cardiovascular diseases and cancer, it affects a large segment of the population and its mechanism(s) of development is (are) poorly understood. It is now clear that ulcer disease is a complex disorder that is multifactorial and pluricausal in origin. Brooks, F.P., in *Peptic Ulcer Disease: Contemporary Issues in Gastroenterology*, Brooks, F.P., et al., eds., Churchill-Livingston, New York, 1985, 145–151; Szabo, S., *Laboratory Investigations* 51:121–147 (1984). The multifactorial etiology and pathogenesis imply that it is unrealistic to expect a complete healing or a preventive effect from highly specific drugs that affect only one component in this complex chain of events. It is thus not surprising that after cessation of treatment with even the currently most potent antisecretory agent (the $H_2$ receptor antagonists such as cimetidine), the recurrence rate of chronic duodenal ulcers is 40–60% a year. Thomas, J.M., et al., *Clin. Gastroenterol.* 13:501–541 (1984). Novel drugs which affect more than one element in the pathogenesis of ulcer disease are thus realistically expected to have a more profound effect on ulcer healing and recurrence than presently available anti-ulcer drugs. "Future research must address the different etiologies of gastric and duodenal ulcers and other acid-peptic conditions, as well as attempting to cure the disease, rather than simply heal the ulcer." Garner, A., *Scand. J. Gastroenterol.* 21, Suppl. 125, 203–210 (1986).

Gastric cytoprotection is a recently developed concept of ulcer treatment that attempts to cure the disease, rather than attack the symptoms. This concept has resulted in the development of new compounds that protect the gastric mucosa. As originally defined, gastric "cytoprotection" referred to several specific modalities that prevent or treat hemorrhagic gastric erosions without inhibiting acid secretion. Examples of these specific modalities include: the prostaglandins (Miller, T.A., *Amer. J. Physiol.* 245:G601–623 (1983)); sulfhydryl group-containing drugs that protect animals from ethanol-induced gastric erosions (Szabo, S., et al., *Science* 214:200–202 (1981)); and certain other agents.

Additional evidence of the involvement of sulfhydryl groups in gastric "cytoprotection" is provided by reports that the protection afforded by prostaglandins and sulfhydryls (Szabo, S., et al., *Science* supra at 201); Szabo, S., *Klin. Wochenschr.* 64, Suppl. VII, 116–122 (1986)), diethylmaleate (Dupuy, D., et al., *Digestion* 31:165 (1985)), polyamines (MiZui, T., et al., *Japan J. Pharmacol.* 33:939–945 (1983)), and sodium salicylate (Ezer, E., *Digestion* 31:168 (1985)) can be counteracted by the irreversible sulfhydryl blocker, N-ethylmaleimide. Further, it has been reported (Dupuy, D., et al., *Gastroenterology* 91:966–977 (1986)) that divalent heavy metal ions that oxidize or bind to sulfhydryl groups (Friedman, M., *The Chemistry and Biochemistry of the Sulfhydryl Groups in Amino Acids*, Oxford: Pergamon, 1973, 25–39) protect animals against ethanol-induced gastric mucosal erosions.

More recently, cytoprotective or gastroprotective drugs are being classified more generically as agents with unknown or multiple (e.g., prosecretory effects for bicarbonate or mucus, vasoprotection, etc.) mechanisms of action. Weinstein, W., *Drug Therapy*, Suppl. 23–27 (1985); Szabo, S., *Gastroenterology* 88:228–236 (1984); Szabo, S., et al., *Gastroenterology* 91:966–974 (1986). The most important practical benefit of the concept of gastric cytoprotection is that it stimulates a focus on novel types of antiulcer agents, i.e., drugs that exert gastroprotective or enteroprotective effects by multiple mechanisms of action, without suppressing normal body functions such as gastric and enzyme secretion. The subject matter of the present invention relates to such unique drugs.

SUMMARY OF THE INVENTION

The present invention is based upon the inventor's consideration that administration of chemical compounds that provide cytoprotection of gastrointestinal mucosal cells to subjects with gastrointestinal ulcer disease would prevent or cure such disease.

The particular anti-ulcer drugs that are the subject of the invention are based upon the inventor's unique observations that: injury to mucosal surface capillaries precedes the development of the hemorrhagic erosions of ulcer disease; vascular injury may be due, at least in part, to the release of proteinases from damaged epithelial cells; and, chemical compounds known to inhibit the activity of proteinases (as exemplified by serine proteinases, thiol proteinases, carboxyl proteinases, and metalloproteinases) have profound cytoprotective effects both in vitro and in vivo, and are efficacious against gastrointestinal ulcer disease in mammals.

These and other objects of the invention, which will hereinafter become more readily apparent, have been obtained by administering to animals suffering with gastrointestinal ulcer disease one or more proteinase inhibitors in doses and under a regimen that prevents or cures the underlying ulcer disease.

DESCRIPTION OF THE PREFERRED EMBODIMENTS

The invention comprises administration of proteinase inhibitors that have beneficial effects on gastrointestinal ulcer disease in mammals.

By the term "gastrointestinal ulcer disease" is intended gastrointestinal injuries in mammals that include, but are not limited to: hemorrhagic and nonhemorrhagic gastric cell injuries due to ingestion of alcohol and aspirin-like drugs; gastric and duodenal ulcer diseases of nonspecific etiology, i.e., idiopathic; ulcerogenic amine-induced duodenal ulcers such as from cysteamine; alkyl-nitrile-induced duodenal ulcers such as from proprionitrile: duodenal ulcers resulting from ingestion of dopamine antagonists (e.g., haloperidol, pimizide, butaclamol, and flupenthixol); duodenal ulcers resulting from ingestion of dopaminergic neurotoxins (e.g., 1-methyl-4-phenyl-1,2,3,6-tetrahydropyridine and its derivatives and metabolites); duodenal ulcers due to inhibitors of tyrosine hydroxylases (e.g., alpha-methyl-p-tyrosine); gastric ulcers due to suppression of bicarbonate production in the face of increased production of gastric acid and pepsin; duodenal ulcers due to an improper mix of acid and base in the duodenal bulb; and, in general, gastroduodenal or small intestinal ulcers induced by ingestion of ulcerogenic chemicals and drugs.

By the term "proteinase" is intended a proteolytic enzyme, that is, one that hydrolyzes a peptide (amide) bond of a protein or polypeptide producing a carboxyl group at the C-terminal end of one fragment and an amino group at the N-terminal end of the other fragment.

The term "proteinase" is intended to include the four major catalytic classes—serine proteinase, cysteine proteinase, carboxyl proteinase and metallo proteinase. Laskowski, M., et al., *Ann. Rev. Biochem.* 49:593–626 (1983).

By the term "serine proteinase" is intended a proteinase that contains a serine residue and a histidine residue at the catalytic center. Examples include, but are not limited to, trypsin, chymotrypsin, cathepsin G, thrombin, plasmin, elastase, tissue kallikrein, factor Xa, factor XIa, collagenase and urokinase.

By the term "cysteine proteinase" is intended a proteinase that contains a cysteine residue at the active center of the enzyme. Examples include, but are not limited to, papin, cathepsin C and cathepsin B.

By the term "carboxyl proteinase" is intended a proteinase that requires a free carboxyl group for activity and that has a pH optimum below about 5. Examples include, but are not limited to, pepsin, cathepsin D and cathepsin E.

By the term "metallo proteinase" is intended a proteinase that uses a metal ion in the catalytic mechanism. Examples include, but are not limited to, collagenase, carboxypeptidase A, carboxypeptidase B, and aminopeptidase.

By the term "proteinase inhibitor" is intended any composition of matter, naturally occurring or synthetic, that decreases or eliminates the catalytic activity of a proteinase. Types of proteinase inhibitors to be administered can be selected by reference to specific inhibitors of catalytic classes of proteinases (e.g., serine, cysteine, carboxyl, and metallo proteinases).

Synthetic proteinase inhibitors include, but are not limited to: phenylmethylsulfonylfluoride, methanesulfonylfluoride, dimethyldichlorovinylphosphate, o-phenanthroline, p-hydroxymercuribenzoate, para-aminobenzamide, iodoacetic acid and its amide, and ethylenediamine tetraacetate.

Naturally occurring proteinase inhibitors include, but are not limited to: aprotinin, leupeptin, pepstatin (Walker, B., *Biochem. Soc. Trans.* 14:397–399 (1986), which is herein incorporated by reference to the extent that it discloses proteinase inhibitors); the human alpha-cysteine proteinase inhibitors of plasma (Gournaris, S.D., et al., *Biochem. J.* 221:445–452 (1984)) and tissue (Green, G.D.J., et al., *Biochem. J.* 218:939–946 (1984)) and urine (Abrahamson, M., et al., *J. Biol. Chem.* 264:11282–11289 (1986); "stefin," the cytosolic protein inhibitor of cysteine proteinases isolated from human polymorphonuclear granulocytes (Nachleidt, W., et al., *Hoppe-Seyler's Z. Physiol Chem.* 364:1475–1486 (1983)); peptide epoxides that inhibit the calcium-activated cysteine proteinase (Calpain II) of intestinal smooth muscle (Parkess, C., et al., *Biochem. J.* 230:509–516 (1985); carboxy-modified amino acids and peptide inhibitors of cathepsin C (the thiol proteinase-dipeptidylaminopeptidase-I (E.C. 3.4.14.1), but not of the serine proteinase chymotrypsin nor of the metalloproteinase leucine aminopeptidase (Thomson, S.A., et al., *J. Med. Chem.* 29:101–111 (1986)); alpha-1-proteinase inhibitor, antithrombin, alpha2-antiplasmin, alpha$_1$-anti-chymotrypsin, alpha$_2$-macroglobulin, inter alpha-trypsin inhibitor, beta$_1$-anticollagenase, and alpha-cysteine proteinase inhibitor (Travis J., et al., *Ann. Rev. Biochem.* 52:655–709 (1983); and, a series of specific proteinase inhibitors summarized by Laskowski, M et al., *Ann. Rev. Biochem.* 49:593–626 (1980) which is herein incorporated by reference.

The term "proteinase inhibitor" further includes, for the intended purpose of this invention, compounds which are structurally similar to the already known natural and synthetic proteinase inhibitors but which vary by one or more chemical moieties and still retain an essentially equivalent biological activity. Such compounds are termed "analogues" in the following.

It is an important feature of the subject invention that one need not inhibit gastrointestinal cysteine proteinases with irreversible sulfhydryl reagents such as iodoacetic acid or its amide. Rather, one may employ any of the aforementioned naturally occurring and synthetic inhibitors of cysteine proteinases and their analogues, as well as inhibitors isolated from gastric and intestinal mucosal tissues themselves, which will ultimately be removed by the host's normal metabolic processes.

It is also a feature of the invention that additional mechanism-based proteinase inhibitors can be selected and prepared by those skilled in the art by established methods. See Walker, B., *Biochem. Soc. Trans.* 14:397–399 (1986), which is herein incorporated by reference to the extent that it discloses methods of preparing proteinase inhibitors. For example, serine proteinases such as trypsin and chymotrypsin can be inhibited by mechanism-based peptides such as tripeptides containing a C-terminal arginylchloromethane, a lysine analog 1-(N-6-amino-n-hexyl)-carbamoylimidazole, and haloenol lactones.

Several animal model systems for the purpose of testing proteinase inhibitors for potential antiulcerogenic properties are well known to those who are skilled in the art. Acute gastric cytoprotection is determined in standard alcohol, acetic acid, and aspirin animal models. Szabo, S., et al., *Gastroenterology* 88:228–236 (1985) and Szabo, S., et al., *J. Pharm. Meth.* 13:59–66 (1985), which are hereby incorporated by reference to the extent that these reports disclose methods of creating and using such animal models. Beneficial effects on acute or chronic duodenal ulcers can be assessed in animal models of acute or chronic duodenal ulcer induced by cysteamine. Szabo, S., *Amer. Jour. J. Pathol.* 93:273–276 (1978) which is herein incorporated by reference to the extent that the report discloses the method and use of such an animal model.

Anti-ulcerogenic proteinase inhibitors are given by mouth twice daily to test animals with established acute duodenal ulcers. Both unselected heterogeneous (gastric and duodenal) ulcers (Szabo, S., *Amer. J. Pathol.* 93 273–276 (1978)) and homogeneous ulcers are used after animals undergo laparotomy on the second day after cysteamine administration in order to create groups of test animals with uniform (e.g., grades 2 or 3) ulcers. Poulsen, S.S., et al., *Digestive Disease Science* 30:161–167 (1985). Chronic gastric ulcers are also induced by oral administration of acetic acid to test animals. Test animals are killed, 10, 21, or 60 days after induction of ulcers and administration of proteinase inhibitors to evaluate ulcer healing. Erosions are rated by computerized planimetry (Szabo, S., et al., *J. Pharmacol. Meth.* 13:59–66 (1985)) on a scale of 0 to 3, with 0 representing normal tissue, 1 indicating 1–4 small petechiae, 2 indicating 5 or more petechiae or hemorrhagic streaks up to 4 mm, and 3 indicating erosions larger than 5 mm or confluent hemorrhages. Standardized tissue sections are processed for light microscopic examination (i.e., histology of formalinfixed, paraffin-embedded sections stained with hematoxylin and eosin or PAS).

Proteinase inhibitors are tested for cytoprotective effects in vitro by methods well known to the art. Monolayer cell cultures of endothelial cells or of other cells of the gastric mucosa (e.g., mucous, parietal, chief, and mast cells, Lewin, N.J.M., et al., in Pretlow, T.G., et al., eds., *Cell Separation: Methods and Selected Applications,* Academic Press, New York, 1982, 223–244) are tested for protection against ulcerogenic substances (e.g., alcohol, hydrochloric acid, aspirin), afforded by proteinase inhibitors added to cell cultures. Cell viability is tested by standard methods, such as counting of intact cells under light microscope and standard dye exclusion or fluorescence tests (e.g., Trypan blue, ethidium bromide).

By the term "administration" is intended introduction of proteinase inhibitors to subjects by any appropriate means known to the medical art, including, but not limited to, oral, enteral, parenteral (e.g., intravenous or subcutaneous), intranasal, or rectal routes.

By the term "treating" is intended the administration to subjects of proteinase inhibitors for purposes which may include prophylaxis, amelioration, prevention or cure of gastrointestinal ulcer disease.

Amounts and regimens for the administration of proteinase inhibitors can be determined readily by those with ordinary skill in the clinical art of treating gastrointestinal ulcer disease. Generally, the dosage of proteinase inhibitor treatment will vary depending upon considerations such as: type of proteinase inhibitor employed; age, condition, gender and extent of the disease in the patient; counterindications, if any, and other variables to be adjusted by the individual physician. Dosage can vary, with a typical dosage comprising 0.05 to 50 mg/kg/day, with a more preferred range being 0.1 to 30 mg/kg/day.

The compounds of the invention can be administered in any appropriate pharmacological carrier for oral, intranasal, rectal or parenteral administration. They can be administered in any form that effects prophylactic, palliative, preventative or curing conditions of gastrointestinal ulcer disease in humans and animals.

The proteinase inhibitors of the invention can be employed in dosage forms such as tablets, capsules, powder packets, or liquid solutions for oral administration. Preparation for parenteral administration include sterile aqueous or non-aqueous solutions, suspensions and emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medical parenteral vehicles including sodium chloride solution, Ringer's dextrose, dextrose plus sodium chloride solution, Ringer's solution containing lactose, or fixed oils. Intravenous vehicles include fluid and nutrient replenishers, electrolyte replenishers, such as those based upon Ringer's dextrose and the like. Rectal vehicles include suppositories containing a pharmacologically inert carrier such as one comprising cocoa butter, glycerinated gelatin, hydrogenated vegetable oils, mixtures of polyethylene glycols of various molecular weights, and fatty acid esters of polyethylene glycol.

Having now generally described the invention, the same may be more readily understood by reference to the following examples, which are not intended to be limiting unless so stated.

EXAMPLE 1

Female Sprague-Dawley rats (150–200 g) from Taconic Laboratory Animals, Inc. (Germantown, N.Y.) initially had unlimited access to Purina Laboratory Chow (Ralston-Purina, St. Louis, Mo.) and tap water, but were fasted overnight before experiments. Rats were used in groups of 3. Each experiment was performed at least twice, and the results were pooled.

The animals received either 0.2, 1, or 10 mg/100 g per os by gavage with a rubber stomach tube (Rusch No. 8) 30 minutes before administering 1 ml of 100% ethanol, also administered per os. Control rats received the same 1 ml of 100% ethanol, per os, but received no inhibitor of cysteine protease.

One hour after ethanol administration, rats were killed by cervical dislocation and the stomach and duodenum were removed and opened along the greater curvature. The stomachs were pinned flat on cork and fixed in 10% buffered formalin. The extent of gastric mucosal damage was measured by stereomicroscopic morphometry using a computerized planimeter (Microplan II, Laboratory Computer Systems, Cambridge, Mass.). The area of mucosal damage was calculated in square millimeters and expressed as percentage of the surface of the glandular stomach (Szabo, S., et al., *J. Pharm. Meth.* 13:59–66 (1985)). Six standard sections from the stomach were embedded in paraffin, cut, and stained with hematoxylin and eosin.

The area of hemorrhagic gastric erosions and ulcers was reduced from 14.9% of glandular stomach in rats receiving only ethanol to 0.4%, 0%, and 0%, respectively, after doses of iodoacetate.

EXAMPLE 2

Two other cysteine protease inhibitors, paraaminobenzamide and para-aminobenzamide, diamide were studied, utilizing the experimental procedures set forth in Example 1. These two compounds demonstrated equal effectiveness against ethanol.

EXAMPLE 3

Leupeptin and phenyl-methyl-sulfonylfluoride, serine protease inhibitors, were also studied, utilizing the experimental procedures set forth in Example 1. Both leupeptin and phenyl-methyl-sulfonylfluoride decreased the ethanol-induced gastric lesions by about 50%.

EXAMPLE 4

Utilizing an essential equivalent experimental procedure to that disclosed in Example 1, the antiulcerogenic effect of iodoacetate was studied with regard to hemorrhagic gastric erosion induced by 0.6 N HCl (1 ml, p.o.) and 0.2 N NaOH (1 ml, p.o.). The control group received no iodoacetate; in those animals receiving iodoacetate, the compound was delivered 30 minutes prior to administration of the ulcer-inducing chemical. Iodoacetate administered at 1 mg/100 g body weight p.o. abolished the ulcerogenic effect of both the 0.6 N HCl and the 0.2 N NaOH.

EXAMPLE 5

The pathogenesis of chemically induced gastric mucosal injury seems to involve at least three pathways. Fasted Sprague-Dawley female rats (150-200 g) received intragastrically 1 ml of 100% ethanol, 0.6 N HCl or 0.2 N NaOH. To detect vascular injury, 3% monastral blue was injected i.v. 3 minutes before autopsy. Evaluation of gastric injury was effected utilizing the technique described in Example 1 above. After administration of 1 ml of ethanol, 1.2, 1.8, 3.4, 26.7, or 29.4% of the glandular stomach showed vascular labeling while hemorrhagic lesions involved 0, 0.1, 0.7, 4.0, or 17.7% of glandular mucosa at 5, 15, 30, 60, or 180 seconds, respectively. Vascular injury also preceded the hemorrhagic lesions after HCl or NaOH.

Laser-Doppler velocimetry demonstrated hypoperfusion and stasis 1-3 minutes after intragastric administration of chemicals.

To determine the role of thiol proteases in gastric injury, the specific activity of cathepsin B was measured in gastric perfusate collected at 1 minute intervals before and after giving 1 ml of ethanol. In 1 minute, the ethanol caused a massive enzyme release. This and the hemorrhagic erosions were abolished by the cysteine protease inhibitor iodoacetate (1 mg/100 g p.o.).

Having now generally described the invention, it will become readily apparent to those skilled in the art that many changes and modifications can be made thereto without affecting the spirit and scope thereof.

What is new and claimed and intended to be covered by Letters Patent is:

1. A method of treating an animal with gastrointestinal ulcer disease induced by an ulcerogenic chemical or drug comprising administration of a cysteine proteinase inhibitor or an analogue thereof to said animal in an amount sufficient to ameliorate or eliminate said disease.

2. A method of preventing gastrointestinal ulcer disease induced by an ulcerogenic chemical or drug in an animal comprising administration of a cysteine proteinase inhibitor or an analogue thereof to said animal in an amount sufficient to prevent said disease.

3. The method of claim 1 or 2 wherein said animal is a human.

4. The method of claim 1 or 2 wherein said ulcerogenic chemical is selected from the group consisting of non-steroidal anti-flammatory drugs and ethanol.

5. The method of claim 4 wherein said non-steroidal anti-inflammatory drug is aspirin.

6. The method of claim 1 or 2 wherein said cysteine proteinase inhibitor is synthetic.

7. The method of claim 1 or 2 wherein said cysteine proteinase inhibitor is naturally-occurring.

8. The method of claim 1 or 2 wherein said cysteine proteinase inhibitor is a metalloproteinase inhibitor.

9. The method of claim 1 or 2 wherein said proteinase inhibitor is administered to said animal by a parenteral route.

10. The method of claim 1 or 2 wherein said proteinase inhibitor is administered to said animal by an intranasal route.

11. The method of claim 1 or 2 wherein said proteinase inhibitor is administered to said animal by a rectal route.

12. The method of claim 1 or 2 wherein said proteinase inhibitor is administered to said animal by an enteral route.

* * * * *